United States Patent
Elsner et al.

(10) Patent No.: US 6,236,877 B1
(45) Date of Patent: May 22, 2001

(54) APPARATUS FOR NEAR SIMULTANEOUS OBSERVATION OF DIRECTLY SCATTERED IMAGE FIELD AND MULTIPLY SCATTERED IMAGE FIELD

(75) Inventors: Ann E. Elsner, Reading; Robert H. Webb, Lincoln, both of MA (US); Andreas W. Dreher, Escondido, CA (US)

(73) Assignees: The Schepens Eye Research Institute, Boston, MA (US); Laser Diagnostics Technologies, Inc., San Diego, CA (US)

( * ) Notice: Subject to any disclaimer, the term of this patent is extended or adjusted under 35 U.S.C. 154(b) by 0 days.

(21) Appl. No.: 09/016,112

(22) Filed: Jan. 30, 1998

(51) Int. Cl.$^7$ ........................................... A61B 5/05
(52) U.S. Cl. ..................... 600/407; 600/473; 600/476; 356/342; 351/221
(58) Field of Search .................... 600/407, 473, 600/475, 476, 477, 310, 479, 504, 558; 356/345–347, 360, 342; 351/221, 226, 205

(56) References Cited

U.S. PATENT DOCUMENTS

| | | | |
|---|---|---|---|
| 3,658,405 | * 4/1972 | Pluta | 356/106 |
| 4,213,678 | 7/1980 | Pomerantzeff et al. | 351/7 |
| 4,555,179 | * 11/1985 | Langerholc et al. | 356/342 |
| 4,764,005 | 8/1988 | Webb et al. | 351/205 |
| 4,838,679 | 6/1989 | Bille | 351/205 |
| 4,844,617 | * 7/1989 | Kelderman et al. | 356/372 |
| 5,028,802 | 7/1991 | Webb et al. | 250/571 |
| 5,137,355 | * 8/1992 | Barbour et al. | 356/342 |
| 5,303,709 | 4/1994 | Dreher et al. | 128/665 |
| 5,760,901 | * 6/1998 | Hill | 356/345 |
| 5,770,454 | * 6/1998 | Essenpreis et al. | 436/164 |
| 5,813,987 | * 9/1998 | Modell et al. | 600/473 |
| 5,830,147 | * 11/1998 | Feke et al. | 600/479 |
| 5,886,768 | * 3/1999 | Knopp et al. | 351/212 |
| 5,963,300 | * 10/1999 | Horwitz | 351/209 |
| 5,973,779 | * 10/1999 | Ansari et al. | 356/301 |
| 6,002,480 | * 12/1999 | Izatt et al. | 356/345 |

OTHER PUBLICATIONS

Elsner, A. et al., "Scattered Light Tomography: Instrumentation and Ocular Fundus Data with a Vertical Cavity Surface Emitting Laser," *Vision Science and its Applications*, vol. 1, 86–9 (Jan. 31–Feb. 3, 1997).

Elsner et al., Infrared imaging of sub–retinal structures in the human ocular fundus, Vision Res Jan. 1996; 36(1):191–205(ISSN:0042–6989).*

* cited by examiner

Primary Examiner—Brian L. Casler
(74) Attorney, Agent, or Firm—Foley, Hoag & Eliot, LLP; W. Hugo Liepmann (57) ABSTRACT

An apparatus for separating an image of a target into a directly scattered component and a multiply scattered component by providing a stationary field stop having a first region and associated detector confocal to a point on the target. During a first interval, a light source directs a first beam to the target and the directly scattered component is selected by the first region. During a second interval, the light source directs a second beam to the target and the multiply scattered component us selected by the first region and its associated detector. Alternatively, a light source directs a first beam to the target and the directly scattered component is selected by the first region of the field stop and its associated detector, while the second region and its associated detector select for multiply scattered light.

49 Claims, 4 Drawing Sheets

APPARATUS FOR NEAR SIMULTANEOUS OBSERVATION OF DIRECTLY SCATTERED IMAGE FIELD AND MULTIPLY SCATTERED IMAGE FIELD

FIELD OF THE INVENTION

This invention relates to the field of image processing and in particular, to methods and devices for separating multiply scattered light from directly scattered light.

BACKGROUND OF THE INVENTION

In many imaging applications, the object to be imaged includes a highly remittive layer. When light illuminates such an object, the resulting image consists of a directly scattered component reflected from this highly remittive layer and a multiply scattered component which is scattered from points that are within the object and outside the highly remittive layer. Because the layer is highly remittive, the directly scattered component tends to dominate the image. As a result, it is difficult to capture the multiply scattered component of the image.

An example of an object having a highly remittive layer is the human retina. In the retina, certain structures are visible only by examination of the directly scattered component of the image. These structures cannot be seen clearly by examination of the multiply scattered component. Examples of such structures include small blood vessels and superficial features of the optic nerve head. Conversely, there exist other retinal structures, such as drusen and sub-retinal edema, which are visible to a far greater extent in the multiply scattered component. Some of these structures cannot readily be observed by examination of the directly scattered light. Accordingly, it is desirable to provide an ocular fundus imaging apparatus for permitting an eye-care specialist to switch easily between observation of the directly scattered component and observation of the multiply scattered component of the image.

A known technique for separating an image into its multiply scattered component and its directly scattered component is to illuminate the retina with a point light source and to direct the remitted image field through a field stop confocal to the light source. By providing the field stop with a pinhole aperture, one can observe the directly scattered component of the image. Alternatively, by providing the field stop with an annular opening, one can observe the multiply scattered component of the image. These techniques are described in Elsner A. E., Burns S. A., Weiter J. J., and Delori F. C., *Infrared imaging of subretinal structures in the human ocular fundus,* Vision Research 36, 191–205, 1996.

Using the foregoing technique, one can provide a field stop with a pinhole aperture, observe the directly scattered component of the image, replace the pinhole aperture with an annular aperture, and then proceed to observe the multiply scattered component of the image. By scanning in two dimensions, one can then generate a two-dimensional image which includes only the multiply scattered component and create another image which includes only the directly scattered component. Similarly, by using known techniques of tomography, one can obtain pairs of cross sections, one including only the multiply scattered component and another which includes only the directly scattered component.

In certain opthalmological applications, it is desirable to precisely locate a structure which can be imaged in the multiply scattered component with respect to a known feature observable only in the directly scattered component. For example, it may be useful to know that a particular region of drusen or edema is located near the intersection of two blood vessels.

A disadvantage of the foregoing known technique is that a significant interval elapses between the measurement of the directly scattered component and the subsequent measurement of the multiply scattered component. This interval arises because of the time required to replace the pinhole aperture with an annular aperture.

Using the method described above, one can, in principle, accomplish the task of precisely locating a structure visible in one component relative to a feature visible in the other component by capturing an image of the directly scattered field and then overlaying it on the image of the multiply scattered field. By aligning the image from the multiply scattered component with the image from the directly scattered component, one can then locate a structure visible only in one component relative to a structure visible only in the other component.

In practice, however, the retina is constantly subject to rapid and unpredictable motion. As a result, in the brief interval, referred to as a blanking interval, that elapses as the annular aperture replaces the pinhole aperture, the retina will have moved by some unknown amount. Since a patient cannot eliminate eye movements, the position of the retina during observation of the multiply scattered component will, in general, not be the same as the position of the retina during observation of the directly scattered component. This unpredictable motion of the retina interferes with the reliable alignment of the two images.

The foregoing disadvantage can, in principle, be mitigated by reducing the blanking interval. If the blanking interval is made short enough, the retina will move a negligible amount between the observation of the directly scattered component and the observation of the multiply scattered component.

In practice, however, the mechanical inertia associated with replacing the pinhole aperture with an annular aperture prevents the blanking interval from being made short enough to capture two successive images without noticeable movement of the retina between images. What is necessary and desirable in the art therefore is an apparatus and method for reducing the blanking interval, thereby permitting observation of the directly scattered component and the multiply scattered component of an image field substantially simultaneously.

SUMMARY OF THE INVENTION

In the method and apparatus of the invention, an illumination source directs incident light onto an illuminated target point optically conjugate to a pinhole aperture. Light remitted from this illuminated point forms an image having a directly scattered component and a multiply scattered component. A stationary field stop of constant geometry separates the remitted image into these two constituent components and directs the two components to one or more detectors. As a result, there is no need for the time-consuming change of the field stop geometry. Consequently, the two constituents of the image can be observed substantially simultaneously.

In one embodiment of the invention, the field stop for separating the two constituents of the image includes a first region optically conjugate to the illuminated point and a second region which is adjacent to the first region. The first region is disposed so that primarily directly scattered light is incident upon it. The second region is disposed so that primarily multiply scattered light is incident on it.

In the foregoing embodiment, the second region can be a reflective surface and the first region can be a pinhole aperture in the reflective surface. In this embodiment, the pinhole aperture admits the directly scattered component of the image and the reflective surface adjacent to the pinhole aperture reflects the multiply scattered component of the image. A detector in optical communication with the pinhole aperture detects the directly scattered component passing through the pinhole aperture. Simultaneously, another detector in optical communication with the reflective surface surrounding the aperture detects the multiply scattered component reflected by the reflective surface. In this embodiment, the directly scattered component and the multiply scattered component are detected simultaneously by two different detectors.

Conversely, the foregoing embodiment can be realized by providing a first region which is a reflective surface and a second region which is an annular aperture surrounding the reflective surface. In this case, the annular aperture admits the multiply scattered component of the image and the reflective surface within the annular aperture reflects the directly scattered component of the image.

The foregoing embodiment can also be realized by providing a first region which is the end of an optical fiber. In this realization of the embodiment, the directly scattered component incident on the end of the optical fiber propagates through the fiber to a detector.

In another embodiment of the invention, time-division multiplexing enables a single detector in optical communication with a pinhole aperture to detect both the directly scattered component and the multiply scattered component of the image. In this embodiment, two sources, a first source optically conjugate to the pinhole aperture and a second source adjacent to the optical conjugate of the pinhole aperture, illuminate adjacent points on the target in alternate intervals.

During a first interval, the first source illuminates the target at a first illuminated point optically conjugate to the pinhole aperture. Directly scattered light from the first illuminated point passes through the pinhole in the field stop to the detector. Meanwhile, the remainder of the field stop blocks the multiply scattered light originating from areas adjacent to or from a volume surrounding the first illuminated point.

During a second interval, the converse occurs. The second source illuminates the target at a second illuminated point optically conjugate to a point adjacent to the pinhole aperture. This second illuminated point is not optically conjugate to the pinhole aperture. Consequently, multiply scattered light, which can originate from areas adjacent to or from a volume surrounding the first illuminated point, passes through the pinhole aperture in the field stop to the detector. Meanwhile, the remainder of the field stop blocks the directly scattered light.

In this embodiment, a single detector receives the directly scattered component and the indirectly scattered component of the image during alternate intervals, without the need to mechanically move or alter the field stop between intervals to switch between the directly scattered mode and the multiply scattered mode. Instead of altering the field stop, this embodiment switches between the directly scattered mode and the multiply scattered mode by electronically switching the illumination source. This electronic switching action can occur much more rapidly than the mechanical switching action associated with altering the geometry of the field stop. In particular, the electronic switching action can occur so rapidly that the retina typically moves by only a negligible amount in the blanking interval between the end of the first interval and the beginning of the second interval.

These and other features, aspects, and advantages of the invention will be better understood with reference to the following description and the accompanying drawings in which:

DETAILED DESCRIPTION

Figure 1:
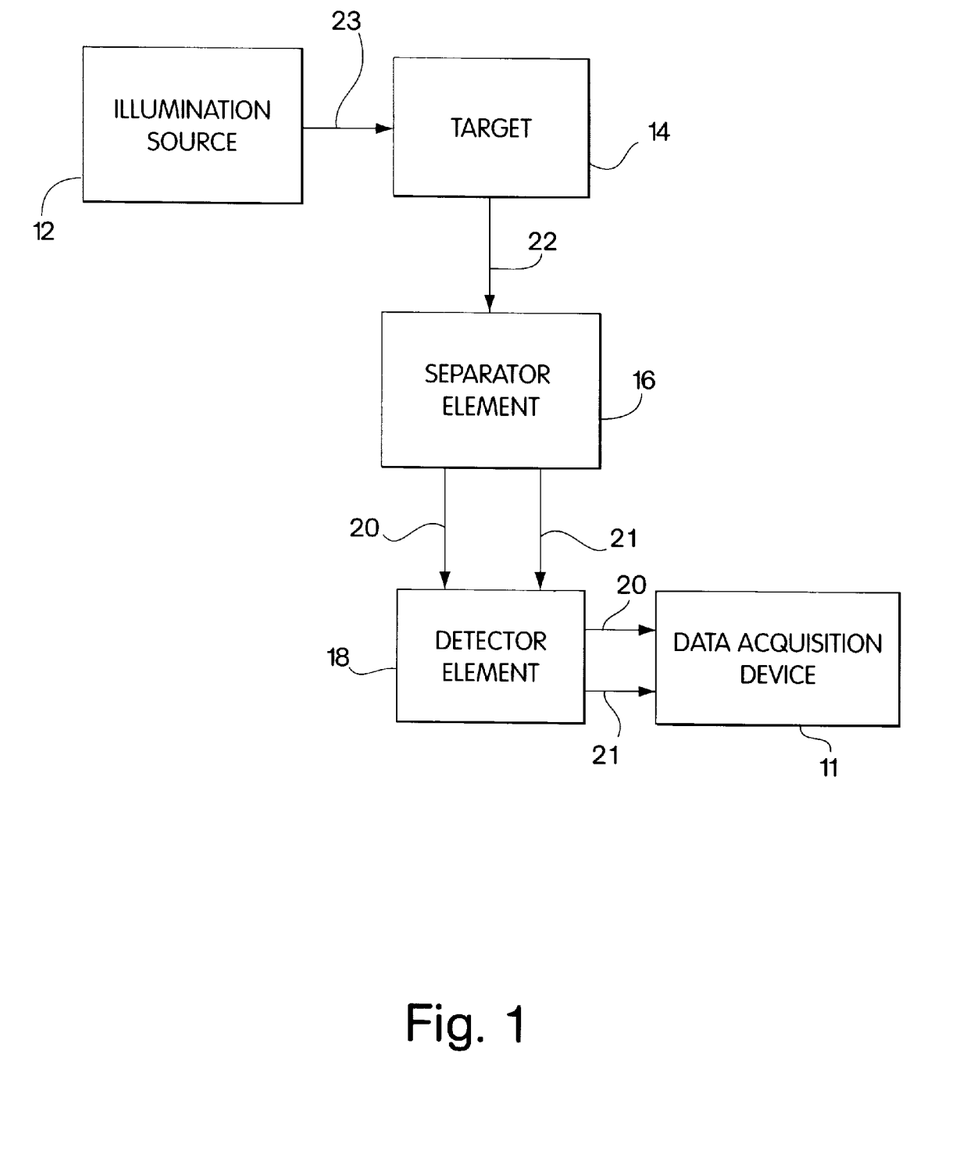
FIG. 1 shows the elements of an imaging system embodying the invention.

Referring to FIG. 1, an optical imaging system 10 embodying the invention includes an illumination source 12 for directing incident light at a target 14. An illuminated point on the target remits light to form an image element 22. The light forming the image element 22 is directed to a stationary image separator 16, which separates it into its constituent components, namely, a multiply scattered image component 21 and a directly scattered image component 20. These constituent components are then directed to a detector element 18 which generates an image from each constituent independently of the other. The two images thus formed are then passed to a data aquisition device 11.

Figure 2:
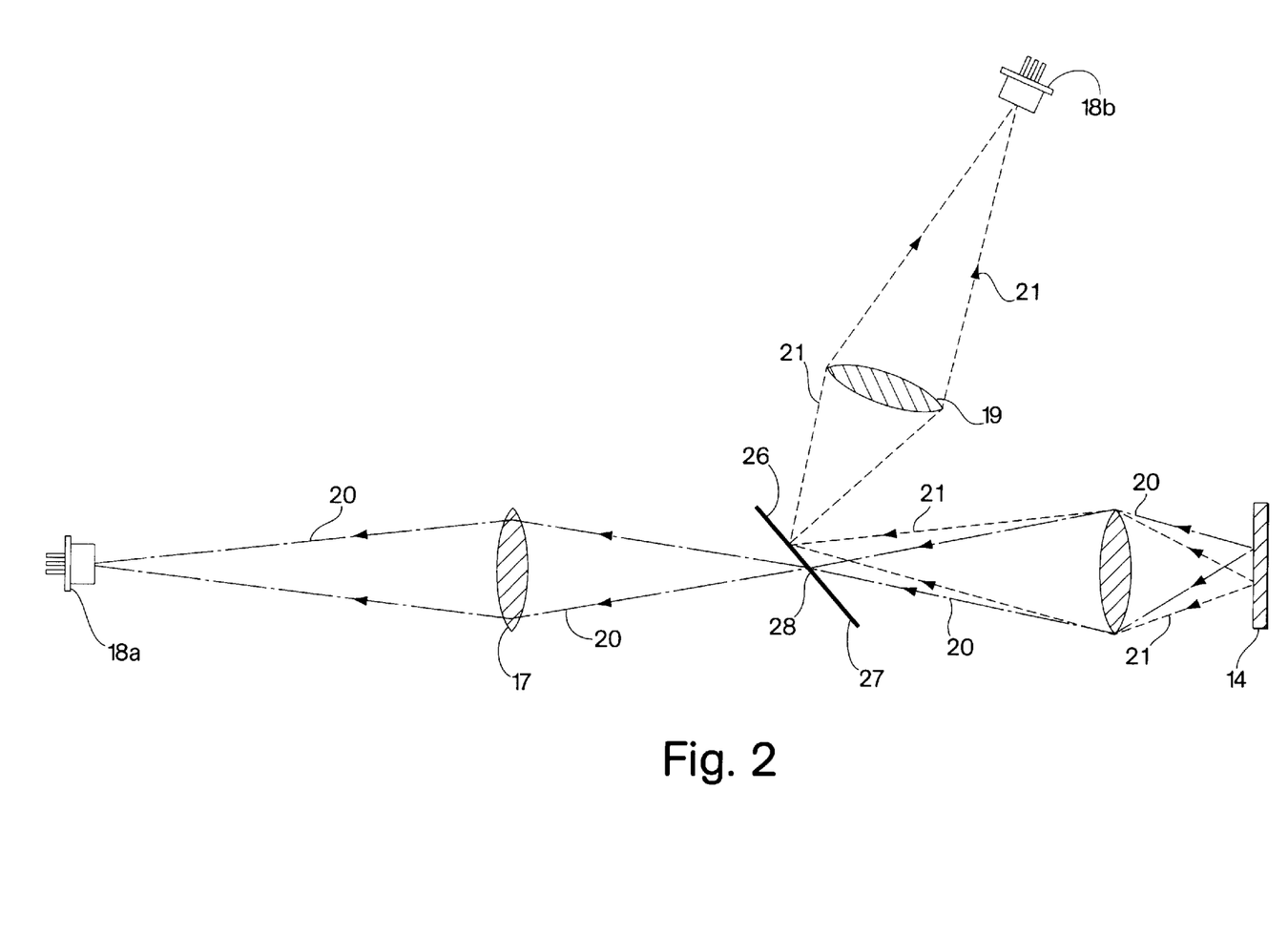
FIG. 2 depicts the paths of the directly scattered component and of the multiply scattered component of the image in one embodiment of the system in FIG. 1.

Referring to FIG. 2, in one embodiment of the invention shown in FIG. 1, the separator element 16 includes a field stop 27 having a pinhole aperture 28 confocal to the illuminated point on the target 14. The face of the field stop facing the target 14 and surrounding the pinhole aperture 28 forms a reflective surface 26 optically aligned to reflect in the direction of a first optical relay system 19. A second optical relay system 17 is oriented to receive target-remitted light passing through the pinhole aperture 28. The detector element 18 in this embodiment includes a first detector 18b in optical communication with the first optical relay system 19 and a second detector 18a in optical communication with the second optical relay system 17.

In operation, a directly scattered image component 20 generated by the illuminated point on the target 14 impinges on the field stop 27. Because the field stop 27 is confocal to the point on the target 14, the directly scattered component, shown as the solid lines in FIG. 2, is focused on the pinhole aperture 28 of the field stop 27. The directly scattered component 20 thus passes through the pinhole aperture 28 and enters the second optical relay system 17. The second optical relay system 17 then directs the directly scattered component to the second detector 18a.

The path followed by multiply scattered component is illustrated by dashed lines in FIG. 2. The multiply scattered component 21 generated by an illuminated target point impinges on the field stop 27, as did the directly scattered component. However, since the multiply scattered component does not originate from points confocal to the pinhole 28, it does not pass through the pinhole. Instead, the multiply scattered component impinges on the reflective surface 26 of the field stop 27. This reflective surface 27 reflects the multiply scattered component 21 to the first optical relay system 19, which in turn directs it to the first detector 18b.

It is apparent from FIG. 2 that the foregoing embodiment decomposes the remitted field 22 into its constituent components, namely the directly scattered component 20 and the multiply scattered component 22, and renders the constituent components observable simultaneously by directing one component to one detector and the other component to another detector.

Figure 3A:
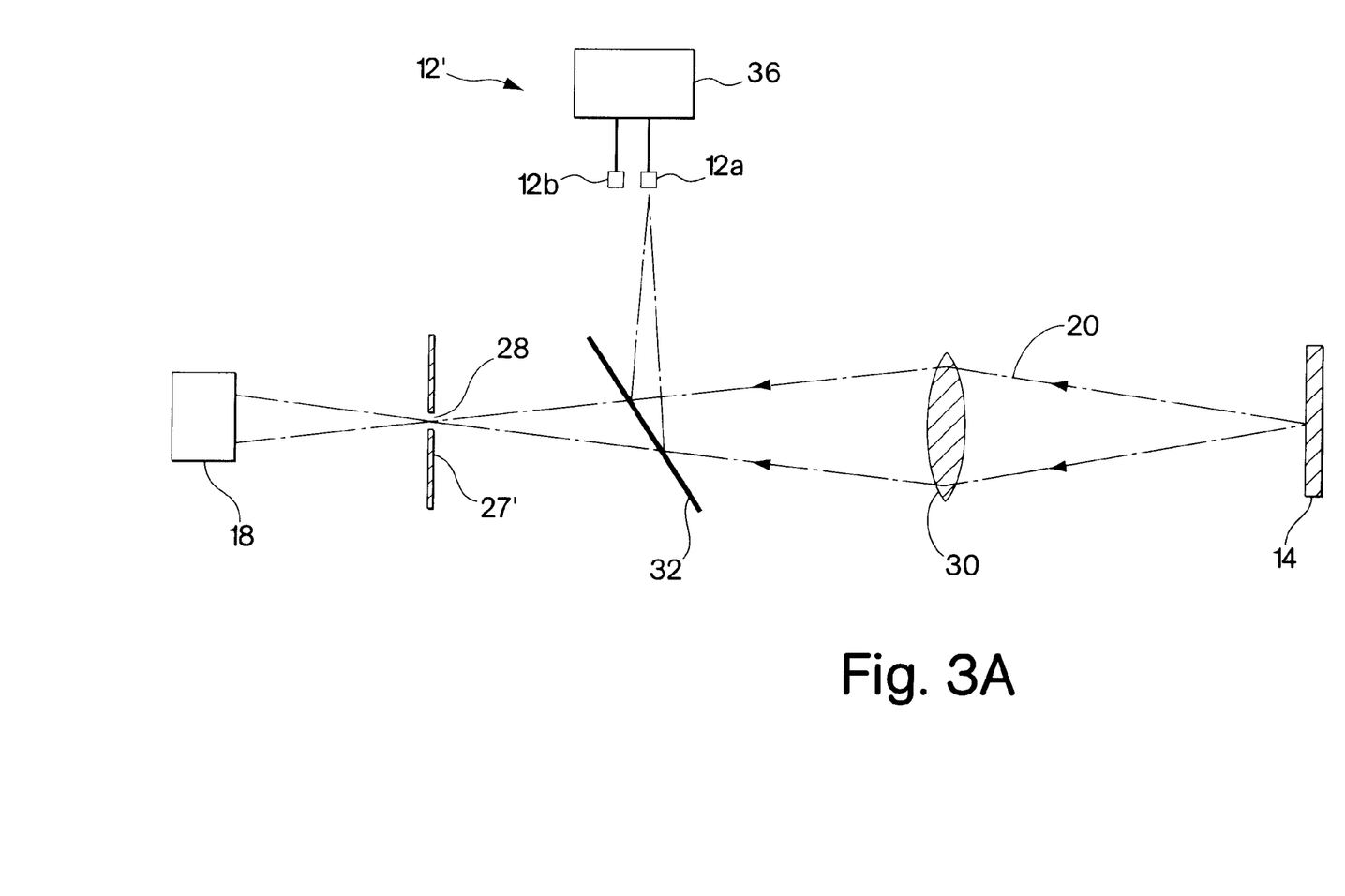
FIG. 3A depicts the path of the directly scattered component of the image in an alternative embodiment of the system in FIG. 1 during a first interval.
Figure 3B:
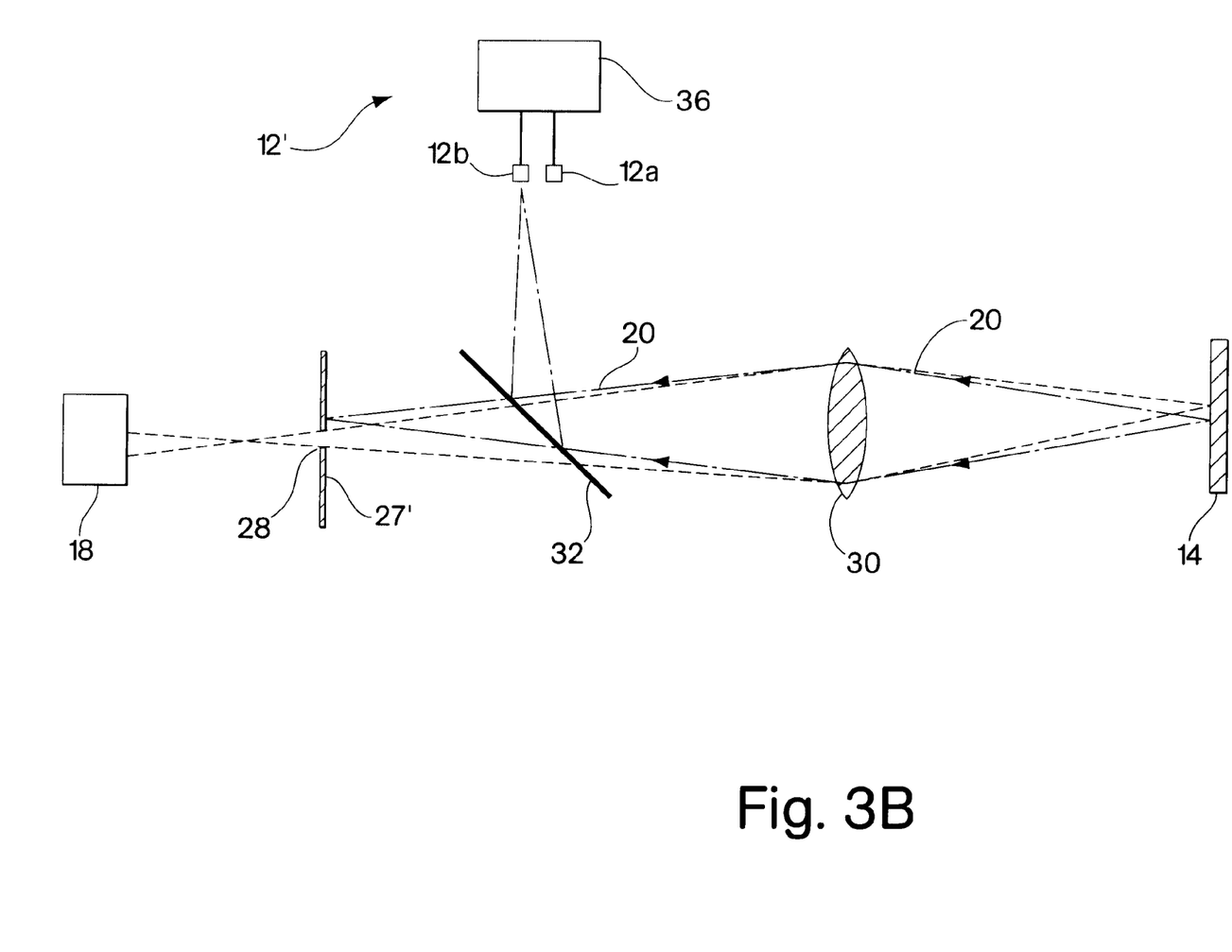
FIG. 3B depicts the paths during a second interval of both the multiply scattered component and the directly scattered component of the image in the embodiment shown in FIG. 3A.

In an alternative embodiment of the FIG. 1 system, in further accord with the invention, shown in FIGS. 3A and 3B, the detector 18 is disposed to receive light from a target 14 through a pinhole aperture 28 in a field stop 27".

The illumination source 12" in this embodiment includes a first light source 12a which is aligned with the optical axis 38 and a second light source 12b which is transversely displaced from the first light source 12a. The light sources 12a, 12b are coupled to a switching circuit 36 for switching between the first light source 12a and the second light source 12b. The illumination source is optically coupled to the target by a beam splitter 32 and by an optical relay system 30. Preferably, the first light source 12a and the second light source 12b are independently addressable lasers in a VCSEL (vertical cavity surface emitting laser) array. Although only two light sources are shown, it will be apparent from the following description of the operation of the imaging device that the illumination source 12" can include a greater plurality of light sources.

In operation, the switching circuit 36 defines a first time interval, during which the detector 18 detects only directly scattered light, and a second time interval during which the detector 18 detects only multiply scattered light.

During the first interval, shown in FIG. 3A, the switching circuit activates the first light source 12a and deactivates the second light source 12b. Light from the first light source reflects off the beam splitter 32 and is directed by the optical relay system 30 to an illuminated point on the target 14. In response to this incident light, the illuminated point remits light. A portion of this light propagates directly back through the optical relay system 30, thereby forming the directly scattered component 20 of the image. Another portion of the light remitted by the illuminated point in response to the incident field scatters off other points within the target, thereby forming the multiply scattered component of the image.

The directly scattered component passes through the optical relay system 30 and through the beam splitter 32. The optical relay system 30 brings this directly-scattered light to a focus at a focal point which is confocal with the illuminated point on the target. During the first interval, this focal point is coincident with the pinhole aperture 28 in the field stop 27". As a result, during the first interval, the directly scattered component passes through the pinhole aperture and reaches the detector 18.

After scattering off the last scattering point in the target, the multiply scattered component also passes through the optical relay system 30. However, unlike the directly scattered component, which originates from a point on the target confocal with the pinhole aperture, this multiply scattered component originates from a point on the target that is not confocal to the pinhole aperture. Thus, the optical relay system 30 brings this multiply scattered component to a focus at a point on the field stop other than the point at which the pinhole aperture is located. In this way, the field stop 27" prevents the multiply scattered component from reaching the detector 18.

As shown in FIG. 3B, during the second interval the switching circuit activates the second light source 12b and deactivates the first light source 12a. Light from the second light source reflects off the beam splitter 32 and is directed by the optical relay system 30 to an illuminated point on the target 14. In response to this incident light, the illuminated point remits light. As was the case in the first interval, a portion of this light propagates directly back through the optical relay system 30, thereby forming the directly scattered component 20 of the image. Another portion of the light remitted by the illuminated point in response to the incident field scatters off other points within the target, thereby forming the multiply scattered component of the image.

As was the case in the first interval, the directly scattered component passes through the optical relay system 30, through the beam splitter 32 and comes to a focus at a focal point which is confocal with the illuminated point on the target. However, because the second light source 12b is displaced from the first light source 12a, this focal point is no longer coincident with the pinhole aperture 28 in the field stop 27. As a result, during the second interval, the field stop blocks the directly scattered component.

After scattering off the last scattering point on the target, the multiply scattered light travels back through the optical relay system 30 and through the beam splitter 32. At least a portion of this multiply scattered light originates at a last scattering point on the target which is confocal with the pinhole aperture. This portion of the multiply-scattered light comes to a focus at a focal point which coincides with the pinhole aperture 28 in the field stop 27 and will therefore pass through the pinhole aperture 28. Thus, light passing through the pinhole will correspond to multiply scattered light. As a result, during the second interval, the detector 18 detects light that is multiply scattered from that point on the target 14 which is confocal to the pinhole aperture.

It is apparent, therefore that the operation of the field stop during the first interval, when the first light source is on and the second source is off, is the converse of its operation during the second interval, when the second light source is on and the first light source is off. During the first interval, the imaging apparatus passes the directly scattered component of the image through the pinhole aperture and blocks the multiply scattered component of the image with the remainder of the field stop. Conversely, during the second interval, the field stop blocks the directly scattered component of the image and admits at least a portion of the multiply scattered component through the pinhole aperture in the field stop.

It is also apparent that by rapidly switching between the state in which the first light source is on and the second light source is off and the converse state in which the second light source is on and the first light source is off, it is possible to view the multiply scattered component and the directly scattered component of the image substantially simultaneously.

It will thus be seen that the invention efficiently attains the objects set forth above. Since certain changes may be made in the above constructions without departing from the scope of the invention, it is intended that all matter contained in the above description or shown in the accompanying drawings be interpreted as illustrative and not in a limiting sense.

It is also to be understood that the following claims are intended to cover all generic and specific features of the invention described herein, and all statements of the scope of the invention which as a matter of language might be said to fall there between. Having described the invention, what is claimed as new and secured by Letters Patent is:

What is claimed is:

1. An imaging apparatus for separating light received from a target into a multiply scattered light component and a directly scattered light component, said apparatus comprising illumination means for directing incident light to a location of said target, thereby generating a multiply scattered light component and a directly scattered light component, separation means for separating said directly scattered light component from said multiply scattered light component, said separation means being a structure stationary relative to said illumination means, and detecting means in optical communication with said separating means for detecting said directly scattered light component and said multiply scattered light component and generating a first image from the directly scattered light component and a second image from the multiply scattered light component.

2. The imaging apparatus of claim 1 wherein said separation means includes a first region optically conjugate to said location, said first region selecting said directly scattered light component, and a second region adjacent to said first region, said second region selecting said multiply scattered light component, and said detection means includes a first detector in optical communication with said first region.

3. The imaging apparatus of claim 2 wherein said first region is a reflective surface and said second region is an aperture.

4. The imaging apparatus of claim 2 wherein said first region is an aperture and said second region is a reflective surface.

5. The imaging apparatus of claim 2 wherein said first region is the end of an optical fiber.

6. The imaging apparatus of claim 2, wherein the detecting means further includes a second detector in optical communication with said second region.

7. The imaging apparatus of claim 2, wherein said first region comprises a reflective surface and said second region comprises an aperture.

8. The imaging apparatus of claim 2, wherein said first region comprises an aperture and said second region comprises a reflective surface.

9. The imaging apparatus of claim 2, wherein said first region comprises the end of an optical fiber.

10. The imaging apparatus of claim 1 wherein
    said illumination means includes
        a first light source and
        a second light source displaced from said first light source, and
    said separation means includes
        a first region optically conjugate to said first light source, and
        a second region adjacent to said first region.

11. The imaging apparatus of claim 10 wherein said first region is a reflective surface.

12. The imaging apparatus of claim 10 wherein said first region is an aperture.

13. The imaging apparatus of claim 10 wherein said first region is the end of an optical fiber.

14. The imaging apparatus of claim 10 wherein said first and second light sources are lasers.

15. The imaging apparatus of claim 10 wherein said first and second light sources are vertical cavity surface emitting lasers.

16. The imaging apparatus of claim 10 further comprising switching means for switching between a first interval during which said first light source is turned on and said second light source is turned off and a second interval during which said second light source is turned on and said first light source is turned off.

17. The imaging apparatus of claim 10, wherein each of said first and second light sources comprises a laser.

18. The imaging apparatus of claim 10, wherein said first and second light sources comprise a vertical cavity surface emitting laser array.

19. The imaging apparatus of claim 1 wherein said illumination means comprises an array of vertical cavity surface emitting lasers.

20. The imaging apparatus of claim 1, further comprising optics means for directing light from the light source to the location of the target.

21. The imaging apparatus of claim 1, wherein the detecting means detects said directly scattered light component and said multiply scattered light component substantially simultaneously.

22. The imaging apparatus of claim 1, wherein the detecting means comprises a first detector for detecting said directly scattered light component and a second detector for substantially simultaneously detecting said multiply scattered light component.

23. The imaging apparatus of claim 1, wherein the detecting means individually detects said directly scattered light component and said multiply scattered light component.

24. A method for separating light received from a target into a multiply scattered component and a directly scattered component, said method comprising the steps of:

directing incident light to an illuminated point on said target, thereby forming a multiply scattered component and a directly scattered component;

separating said directly scattered component from said multiply scattered component with a stationary separation structure;

detecting said directly scattered component and said multiply scattered component; and generating a first image from the directly scattered component and a second image from the multiply scattered component.

25. The method of claim 24 wherein said separation step includes the steps of selecting said directly scattered component with a first region optically conjugate to said illuminated point and selecting said multiply scattered component with a second region adjacent to said first region; and said detection step includes the steps of detecting said directly scattered component with a first detector in optical communication with said first region; and detecting said multiply scattered component with a second detector in optical communication with said second region.

26. The method of claim 25 wherein said first region is a reflective surface and said second region is an aperture.

27. The method of claim 25 wherein said first region is an aperture and said second region is a reflective surface.

28. The method of claim 25 wherein said first region is the end of an optical fiber.

29. The method of claim 24 wherein
said illumination step includes the step of providing
- a first light source and
- a second light source displaced from said first light source; and said separation step includes the steps of
- illuminating the target with said first light source,
- receiving said directly scattered component with a region optically conjugate to said first light source;
- illuminating said target with said second light source, and
- receiving said multiply scattered component with said region.

30. The method of claim 29 wherein said region is a reflective surface.

31. The method of claim 29 wherein said region is an aperture.

32. The method of claim 29 wherein said region is the end of an optical fiber.

33. The method of claim 29 wherein said first and second light sources are lasers.

34. The method of claim 29 wherein said first and second light sources are vertical cavity surface emitting lasers.

35. The method of claim 29 further comprising the step of switching between a first interval during which said first light source is turned on and said second light source is turned off and a second interval during which said second light source is turned on and said first light source is turned off.

36. The method of claim 24 wherein said incident light is provided by an array of vertical cavity surface emitting lasers.

37. The method of claim 24, wherein said detecting of said directly scattered component and of said multiply scattered component includes substantially simultaneously detecting said directly scattered component and said multiply scattered component.

38. The method of claim 24, wherein said detecting of said directly scattered component and of said multiply scattered component includes detecting said directly scattered component with a first detector and substantially simultaneously detecting said multiply scattered component with a second detector.

39. The method of claim 24, wherein said detecting of said directly scattered component and of said multiply scattered component includes individually detecting said directly scattered component and said multiply scattered component.

40. A method for tomographically imaging a target by separating light received from a target into a multiply scattered component and a directly scattered component, said method comprising the steps of:
- directing incident light to a location of said target, thereby generating a multiply scattered light component and a directly scattered light component,
- separating said directly scattered light component from said multiply scattered light component with a stationary separation structure; and
- detecting said directly scattered light component and said multiply scattered light component and generating a first image from the directly scattered light component and a second image from the multiply scattered light component.

41. The method of claim 40, wherein said detecting of said directly scattered light component and of said multiply scattered light component includes detecting said directly scattered light component with a first detector and substantially simultaneously detecting said multiply scattered light component with a second detector.

42. An imaging device for separating light received from a target into a multiply scattered light component and a directly scattered light component, said apparatus comprising
- a light source to illuminate a target and generate a multiply scattered light component and a directly scattered light component,
- a reflective filter in optical communication with said light source having an aperture to separate said directly scattered light component from said multiply scattered light component,
- a first detector positioned to receive light transmitted through the aperture and generate a first image therefrom, and
- a second detector positioned to receive light reflected by the filter and generate a second image therefrom,
- whereby said multiply scattered light component and said directly scattered light component are detected substantially simultaneously.

43. An imaging device for separating light received from a target into a multiply scattered light component and a directly scattered light component, said apparatus comprising
- a lighting system, comprising a first light source and a second light source displaced from the first light source, to illuminate a target and generate a multiply scattered light component and a directly scattered light component,
- a filter having an aperture to separate said directly scattered light component from said multiply scattered light component, and
- a detector positioned to receive light passing through the aperture and generate a first image from the directly scattered light component and a second image from the multiply scattered light component,
- whereby the directly scattered light generated by the first light source is received by the detector, and the directly scattered light generated by the second light source is blocked by the filter.

44. The imaging device of claim 43, further comprising a switching system coupled to the lighting system to alternate between a first condition wherein a first light source is on and the second light source is off and a second condition wherein the first light source is off and the second light source is on.

45. The imaging device of claim 43, further comprising a light control system for alternating between a first condition wherein the target is illuminated by a first light source and a second condition wherein the target is illuminated by the second light source.

46. A method for separating light received from a target into a multiply scattered light component and a directly scattered light component, said method comprising the steps of
- directing light from a first light source onto a target and thereby generating a multiply scattered light component and a directly scattered light component,
- separating said directly scattered light component from said multiply scattered light component with a filter having an aperture,
- detecting said directly-scattered light component and said multiply scattered light component substantially simultaneously with a light detection system, and generating a first image from the directly scattered light and a second image from the multiply scattered light.

47. The method of claim 46, wherein said separating step comprises reflecting the multiply scattered light component from a reflective surface of the filter and transmitting the directly scattered light component through the aperture of the filter, and said detecting step comprises detecting said directly scattered light component with a first detector positioned to receive light transmitted by the aperture of the filter and substantially simultaneously detecting said multiply scattered light component with a second detector positioned to receive light reflected by the filter.

48. The method of claim 46, further comprising the step of directing light from a second light source onto the target, whereby light projected from the first light source generates directly scattered light that passes through the aperture of the filter, and light projected from the second light source generates directly scattered light that is blocked by the filter.

49. The method of claim 48, further comprising the step of alternating between a first state wherein the first light source is on and the second light source is off and a second state wherein the first light source is off and the second light source is on.

* * * * *